US009770284B2

(12) United States Patent
Behnke, II et al.

(10) Patent No.: US 9,770,284 B2
(45) Date of Patent: *Sep. 26, 2017

(54) SYSTEM AND METHOD FOR DIRECTING ENERGY TO TISSUE

(71) Applicant: COVIDIEN LP, Mansfield, MA (US)

(72) Inventors: Robert J. Behnke, II, Erie, CO (US); Scott E. M. Frushour, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,229

(22) Filed: Jun. 22, 2016

(65) Prior Publication Data

US 2016/0302846 A1   Oct. 20, 2016

Related U.S. Application Data

(63) Continuation of application No. 13/469,960, filed on May 11, 2012, now Pat. No. 9,375,249.

(51) Int. Cl.
| | |
|---|---|
| *A61B 18/18* | (2006.01) |
| *A61B 18/12* | (2006.01) |
| *A61B 18/00* | (2006.01) |
| *A61B 18/14* | (2006.01) |

(52) U.S. Cl.
CPC ...... *A61B 18/1206* (2013.01); *A61B 18/1815* (2013.01); *A61B 18/1442* (2013.01); *A61B 2018/00577* (2013.01); *A61B 2018/00642* (2013.01); *A61B 2018/00785* (2013.01); *A61B 2018/00791* (2013.01); *A61B 2018/00845* (2013.01); *A61B 2018/00875* (2013.01); *A61B 2018/124* (2013.01);

(Continued)

(58) Field of Classification Search
CPC ............... A61B 18/18; A61B 18/1815; A61B 2018/00577; A61B 2018/00636; A61B 2018/00642; A61B 2018/00785
USPC ...................................... 606/33, 34
See application file for complete search history.

(56) References Cited

U.S. PATENT DOCUMENTS

| | | | |
|---|---|---|---|
| 5,558,671 | A | 9/1996 | Yates |
| 5,588,432 | A | 12/1996 | Crowley |
| 5,817,093 | A | 10/1998 | Williamson, IV et al. |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

International Search Report EP09004250.8 dated Aug. 2, 2010.

(Continued)

*Primary Examiner* — Allen Porter, Jr.

(57) ABSTRACT

An electrosurgical system includes an electrosurgical power generating source, an energy applicator operably associated with the electrosurgical power generating source, a processor unit, and a data acquisition module configured to receive a reflected signal. The processor unit is disposed in operative communication with the data acquisition module and adapted to determine a tissue desiccation rate around at least a portion of the energy applicator based on one or more signals received from the data acquisition module.

7 Claims, 8 Drawing Sheets

(52) U.S. Cl.
CPC ............... *A61B 2018/1823* (2013.01); *A61B 2018/1838* (2013.01); *A61B 2018/1869* (2013.01)

(56) References Cited

U.S. PATENT DOCUMENTS

| | | | |
|---|---|---|---|
| 6,190,382 | B1* | 2/2001 | Ormsby ............ A61B 18/1492 606/33 |
| 6,402,741 | B1 | 6/2002 | Keppel et al. |
| 7,137,980 | B2 | 11/2006 | Buysse et al. |
| 7,300,435 | B2 | 11/2007 | Wham et al. |
| 7,364,577 | B2 | 4/2008 | Wham et al. |
| D574,323 | S | 8/2008 | Waaler |
| 7,699,841 | B2 | 4/2010 | Carr |
| 7,749,217 | B2 | 7/2010 | Podhajsky |
| 7,901,400 | B2 | 3/2011 | Wham et al. |
| 9,375,249 | B2 | 6/2016 | Behnke, II et al. |
| 2002/0087156 | A1 | 7/2002 | Maguire et al. |
| 2002/0091427 | A1 | 7/2002 | Rappaport et al. |
| 2004/0002700 | A1 | 1/2004 | Ryan et al. |
| 2007/0013376 | A1* | 1/2007 | Heid ................ A61B 5/055 324/309 |
| 2007/0219548 | A1 | 9/2007 | Carr |
| 2007/0282320 | A1 | 12/2007 | Buysse et al. |
| 2009/0287205 | A1 | 11/2009 | Ingle |
| 2010/0063494 | A1 | 3/2010 | Orszulak |
| 2010/0063497 | A1 | 3/2010 | Orszulak |
| 2010/0094271 | A1 | 4/2010 | Ward et al. |
| 2010/0137857 | A1 | 6/2010 | Shroff et al. |
| 2010/0179538 | A1 | 7/2010 | Podhajsky |
| 2010/0217258 | A1 | 8/2010 | Floume et al. |
| 2011/0071516 | A1 | 3/2011 | Gregg |
| 2011/0319881 | A1 | 12/2011 | Johnston |
| 2013/0267943 | A1 | 10/2013 | Hancock |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 246350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 556705 A1 | 8/1993 |
| EP | 608609 A2 | 8/1994 |
| EP | 836868 A2 | 4/1998 |
| EP | 880220 A2 | 11/1998 |
| EP | 882955 A1 | 12/1998 |
| EP | 1051948 A2 | 11/2000 |
| EP | 1151725 A1 | 11/2001 |
| EP | 1366724 A1 | 12/2003 |
| EP | 1776929 A1 | 4/2007 |
| EP | 1862137 A1 | 12/2007 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| SU | 166452 | 1/1965 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |

OTHER PUBLICATIONS

International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.

(56) References Cited

OTHER PUBLICATIONS

U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, filed May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; 20.sup.th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.

(56) References Cited

OTHER PUBLICATIONS

International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.

\* cited by examiner

SYSTEM AND METHOD FOR DIRECTING ENERGY TO TISSUE

CROSS-REFERENCE TO RELATED APPLICATIONS

This application is a continuation application of U.S. application Ser. No. 13/469,960, filed on May 11, 2012, the entire contents of which are incorporated by reference herein.

BACKGROUND

1. Technical Field

The present disclosure relates to systems, devices and methods for performing a medical procedure. More particularly, the present disclosure relates to electrosurgical systems including a data acquisition module operably associated with an energy applicator and methods of directing energy to tissue.

2. Discussion of Related Art

Electrosurgery is the application of electricity and/or electromagnetic energy to cut, dissect, ablate, coagulate, cauterize, seal or otherwise treat biological tissue during a surgical procedure. When electrical energy and/or electromagnetic energy is introduced to tissue, it produces excitation of molecules, which results in the generation of heat. Generally, electrosurgery utilizes an electrosurgical generator operable to output energy and active and return electrodes that are electrically connected via a cable assembly to the generator. Electrosurgery can be performed using either a monopolar or a bipolar instrument.

Electrosurgical generators are employed by surgeons in conjunction with electrosurgical instruments to perform a variety of surgical procedures. An electrosurgical generator generates and modulates electrosurgical energy which, in turn, is applied to the tissue by an electrosurgical instrument.

Electrosurgical generators may provide energy delivery in two types of modes: continuous and pulsed. The current output of electrosurgical generators can be modulated to deliver different waveforms to the tissue, depending on the mode. As the output waveforms change, so does the corresponding tissue effect. The continuous mode of current output is often referred to as the "cut" mode and delivers electrosurgical energy as a continuous sinusoidal waveform. In addition to the pure "cut" mode, there are often blended modes that modify the degree of current interruption to achieve varying degrees of cutting with hemostasis. Interrupted current generally is quantified by expressing the "on" time as a percentage of the total time, creating a value called the duty cycle.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Tissue effects that can be achieved with electrosurgery can be roughly divided into three basic groups: cutting, fulguration, and desiccation. In addition to output modes and power settings, electrosurgical tissue effects depend on a number of other factors. The size and geometry of the electrodes delivering the energy play a role in achieving the desired surgical effect. Using electrosurgical instruments to ablate, seal, cauterize, coagulate, and/or desiccate tissue may result in some degree of thermal injury to surrounding tissue. For example, electrosurgical desiccation may result in undesirable tissue damage due to thermal effects, wherein otherwise healthy tissue surrounding the tissue to which the electrosurgical energy is being applied is thermally damaged by an effect known in the art as "thermal spread". During the occurrence of thermal spread excess heat from the operative site can be directly conducted to the adjacent tissue, and/or the release of steam from the tissue being treated at the operative site can result in damage to the surrounding tissue. The duration of the activation of the generator is directly related to the heat produced in the tissue. The greater the heat produced, the more the potential for thermal spread to adjacent tissues.

It has been well established that a measurement of the electrical impedance of tissue provides an indication of the state of desiccation of the tissue, and this observation has been utilized in some electrosurgical generators to automatically terminate the generation of electrosurgical power based on a measurement of tissue impedance. At least two techniques for determining an optimal amount of desiccation are known by those skilled in this art. One technique sets a threshold impedance, and terminates electrosurgical power when the measured tissue impedance crosses the threshold. A second technique terminates the generation of electrosurgical power based on dynamic variations in the tissue impedance.

Currently available systems and methods for controlling an electrosurgical generator during electrosurgery may include a clinician monitoring and adjusting, as necessary, the amount of energy delivered to a tissue site through current, voltage, impedance, and/or power measurements such that an appropriate tissue effect can be achieved at the tissue site with minimal collateral damage resulting to adjacent tissue. These systems and/or methods typically require a clinician to translate the desired tissue effect to a power setting on an electrosurgical generator and, if necessary, adjust the power setting to compensate for tissue transformations (e.g., desiccation of tissue) associated with the electrosurgical procedure such that a desired tissue effect may be achieved.

As can be appreciated, limiting the possibility of thermal spread or the like during an electrosurgical procedure reduces the likelihood of unintentional and/or undesirable collateral damage to surrounding tissue structures which may be adjacent to an intended treatment site. Controlling and/or monitoring the depth of thermal spread during an electrosurgical procedure may aid a clinician in assessing tissue modification and/or transformation during the electrosurgical procedure.

SUMMARY

A continuing need exists for systems, devices and methods for controlling and/or monitoring real-time tissue effects to improve patient safety, reduce risk and/or improve patient outcomes.

According to an aspect of the present disclosure, an electrosurgical system is provided. The electrosurgical system includes an electrosurgical power generating source, an energy applicator operably associated with the electrosurgical power generating source, a processor unit, and a data acquisition module configured to receive a reflected signal. The processor unit is disposed in operative communication with the data acquisition module and adapted to determine a tissue desiccation rate around at least a portion of the energy applicator based on one or more signals received from the data acquisition module.

According to another aspect of the present disclosure, a method of directing energy to tissue is provided. The method includes the initial step of positioning an energy applicator for delivery of energy to a target tissue. The energy applicator is operably associated with a data acquisition module. The data acquisition module is operably associated with an electrosurgical power generating source including a processor unit. The method also includes the steps of transmitting energy from the electrosurgical power generating source through the energy applicator to the target tissue, transmitting a signal reflected from the target tissue to the data acquisition module, and determining one or more operating parameters associated with the electrosurgical power generating source based on a tissue desiccation rate determined by the processor unit based on one or more signals received from the data acquisition module.

According to another aspect of the present disclosure, a method of directing energy to tissue is provided. The method includes the initial step of positioning an energy applicator for delivery of energy to a target tissue. The energy applicator is operably associated with an electrosurgical power generating source. The method also includes the steps of transmitting energy from the electrosurgical power generating source through the energy applicator to the target tissue, acquiring data including a frequency of a signal reflected from the target tissue, calculating a tissue desiccation rate as a function of the frequency of the signal reflected from the target tissue, and determining one or more operating parameters associated with the electrosurgical power generating source based on the calculated tissue desiccation rate.

In any one of the aspects, the one or more operating parameters associated with the electrosurgical power generating source is selected from the group consisting of temperature, impedance, power, current, voltage, mode of operation, and duration of application of electromagnetic energy.

BRIEF DESCRIPTION OF THE DRAWINGS

Objects and features of the presently-disclosed data acquisition module operably associated with an energy applicator, electrosurgical power generating source operably associated therewith, and electrosurgical systems including the same, and methods of directing energy to tissue will become apparent to those of ordinary skill in the art when descriptions of various embodiments thereof are read with reference to the accompanying drawings, of which.

DETAILED DESCRIPTION

Hereinafter, embodiments of the presently-disclosed data acquisition module operably associated with an energy applicator, electrosurgical power generating source operably associated therewith, and electrosurgical systems including the same, and the presently-disclosed methods of directing energy to tissue, are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "transmission line"

generally refers to any transmission medium that can be used for the propagation of signals from one point to another.

For the purposes herein, the term "electrosurgical desiccation" or, simply, "desiccation", is intended to encompass any tissue desiccation procedure, including electrosurgical coagulation, desiccation, vessel sealing, and tissue fusion. As it is used in this description, the term "thermal spread" refers generally to the heat transfer (e.g., heat conduction, heat convection or electrical current dissipation) traveling along the periphery of the electrically-conductive, tissue-contacting surfaces.

Various embodiments of the present disclosure provide a data acquisition module operably associated with an energy applicator. Various embodiments of the present disclosure provide electrosurgical systems and instruments suitable for sealing, cauterizing, coagulating/desiccating and/or cutting vessels and vascular tissue, ablating tissue, or otherwise modifying a tissue or organ of a patient, wherein the presently-disclosed data acquisition module receives a reflected signal from an energy applicator and provides a signal used to determine the rate of desiccation of tissue, which, in turn, may be used to determine one or more operating parameters of an electrosurgical power generating source.

Various embodiments of the presently-disclosed electrosurgical systems and instruments use the frequency of a signal reflected from target tissue to determine the rate of desiccation of tissue and/or hydration level of the tissue around at least a portion of an energy applicator. Embodiments may be implemented using electromagnetic radiation at RF or microwave frequencies or at other frequencies.

In accordance with embodiments of the present disclosure, one or more operating parameters of an electrosurgical power generating source are adjusted and/or controlled based on the determined desiccation rate, e.g., to maintain a proper desiccation rate, or to determine when tissue has been completely desiccated and/or the procedure has been completed.

Various embodiments of the presently-disclosed electrosurgical systems employ a secondary frequency, wherein the secondary frequency is different than the primary power source frequency, to determine a type of tissue, a condition of tissue, and/or a tissue response. In accordance with embodiments of the present disclosure, a secondary frequency may be used to assist in determining when the energy applicator has been removed from the target tissue, which may trigger safety procedures and/or controls, e.g., control that reduces power level and/or shuts off the power delivery to the energy applicator.

Figure 1:
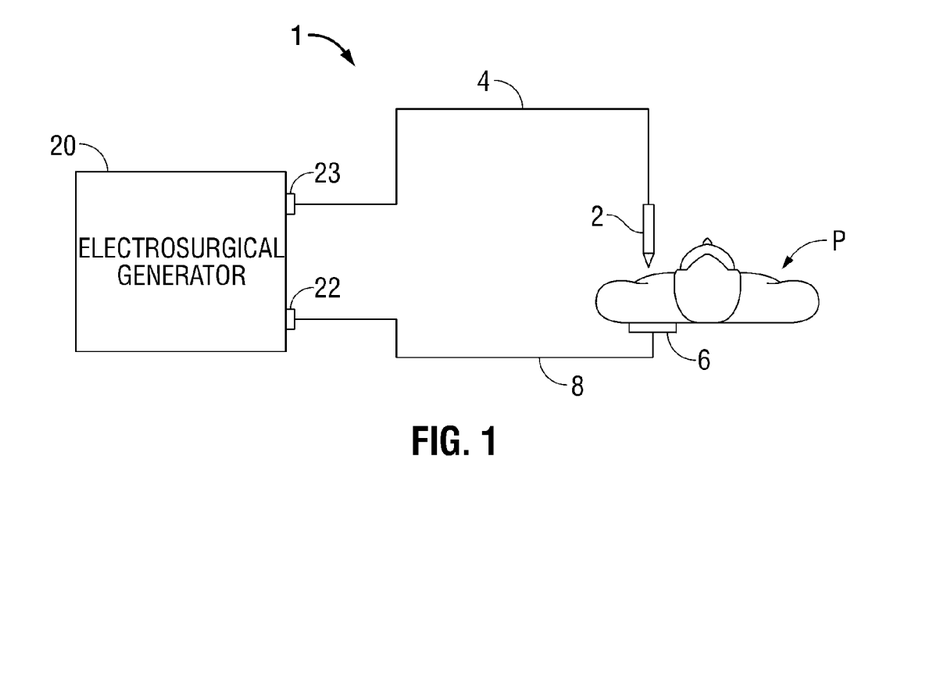
FIG. 1 is a schematic diagram of an electrosurgical system, such as a monopolar electrosurgical system, according to an embodiment of the present disclosure.

FIG. 1 schematically illustrates a monopolar electrosurgical system (shown generally as 1) configured to selectively apply electrosurgical energy to target tissue of a patient P. Electrosurgical system 1 includes a monopolar electrosurgical instrument 2 having one or more electrodes for treating tissue of the patient P (e.g., electrosurgical pencil, electrosurgical cutting probe, ablation electrode(s), etc.). Electrosurgical energy is supplied to the instrument 2 by an electrosurgical power generating source 20 capable of generating. Power generating source 20 may be any generator suitable for use with electrosurgical devices to generate energy having a controllable frequency and power level, and may be configured to provide various frequencies of electromagnetic energy. Power generating source 20 may be configured to operate in a variety of modes, such as ablation, monopolar and bipolar cutting, coagulation, and other modes.

The instrument 2 is connected via a transmission line, e.g., supply line 4, to an active terminal 23 of the electrosurgical power generating source 20, allowing the instrument 2 to coagulate, ablate and/or otherwise treat tissue. The energy is returned to the electrosurgical power generating source 20 through a return electrode 6 via a transmission line, e.g., return line 8, which is connected to a return terminal 22 of the power generating source 20. In some embodiments, the active terminal 23 and the return terminal 22 may be configured to interface with plugs (not shown) associated with the instrument 2 and the return electrode 6, respectively, e.g., disposed at the ends of the supply line 4 and the return line 8, respectively.

The system 1 may include a plurality of return electrodes 6 that are arranged to minimize the chances of tissue damage by maximizing the overall contact area with the patient P. The power generating source 20 and the return electrode 6 may additionally, or alternatively, be configured for monitoring so-called "tissue-to-patient" contact to ensure that sufficient contact exists therebetween to further minimize chances of tissue damage. The active electrode may be used to operate in a liquid environment, wherein the tissue is submerged in an electrolyte solution.

Figure 2:
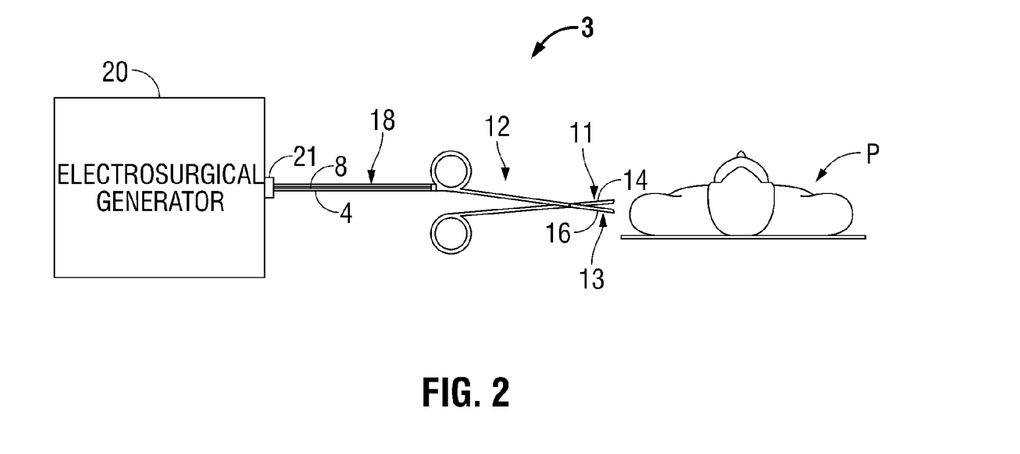
FIG. 2 is a schematic diagram of an electrosurgical system, such as an bipolar electrosurgical system, according to an embodiment of the present disclosure.

FIG. 2 schematically illustrates a bipolar electrosurgical system (shown generally as 3) configured to selectively apply electrosurgical energy to target tissue of a patient P. Electrosurgical system 3 includes a bipolar electrosurgical forceps 12 having one or more electrodes for treating tissue of a patient P. The electrosurgical forceps 12 includes opposing jaw members 11 and 13 including an active electrode 14 and a return electrode 16, respectively, associated therewith. The active electrode 14 and the return electrode 16 are connected to the electrosurgical power generating source 20 through cable 18. Cable 18 may include the supply and return lines 4 and 8 electrically-coupled to the active and return terminals 23 and 22, respectively (shown in FIG. 1). The electrosurgical forceps 10 is coupled to the power generating source 20 at a connector 21 having connections to the active and return terminals 23 and 22 (e.g., pins) via a plug (not shown) disposed at the end of the cable 18, wherein the plug includes electrical contacts associated with the supply and return lines 4 and 8.

Figure 3:
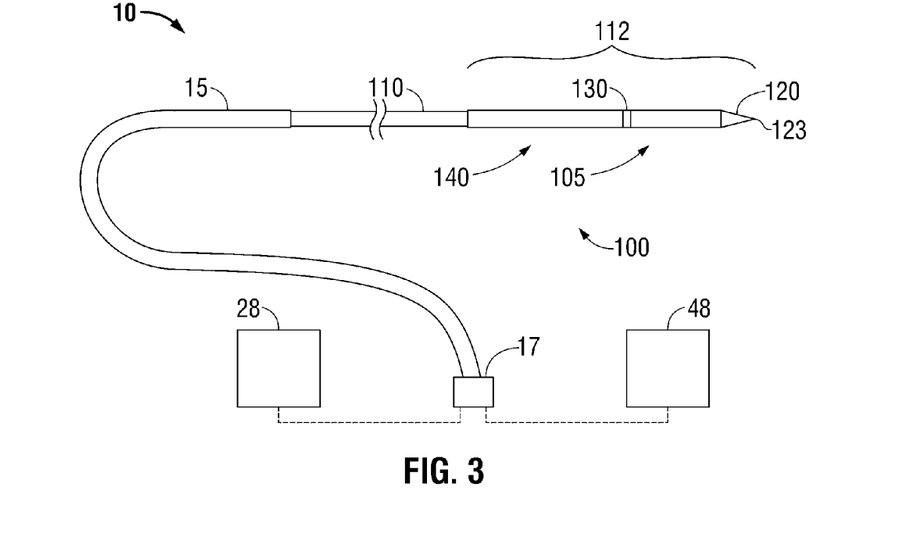
FIG. 3 is a schematic diagram of another embodiment of an electrosurgical system according to the present disclosure.

FIG. 3 schematically illustrates an electrosurgical system (shown generally as 10) including an energy applicator or probe 100. Probe 100 generally includes an antenna assembly 112 having a radiating portion connected by a feedline 110 (or shaft) via a transmission line 15 to a connector 17, which further operably connects the probe 100 to an electrosurgical power generating source 28, e.g., a microwave or RF electrosurgical generator. Power generating source 28 may be any generator suitable for use with electrosurgical devices, and may be configured to provide various frequencies of energy. An embodiment of an electrosurgical power generating source, such as the power generating source 28 of FIG. 3, in accordance with the present disclosure, is shown in more detail in FIG. 6. It will be understood, however, that other power generating source embodiments (e.g., power generating source 500 shown in FIG. 5) may also be used.

Feedline 110 electrically connects the antenna assembly 12 via the transmission line 15 to the electrosurgical power generating source 28, and may include a coaxial cable, which may be semi-rigid or flexible. Feedline 110 may be cooled by fluid, e.g., saline or water, to improve power handling, and may include a stainless steel catheter. Transmission line 15 may additionally, or alternatively, provide a conduit (not shown) configured to provide coolant from a coolant source 18 to the probe 100.

Antenna assembly 112, as shown in FIG. 3, is a dipole microwave antenna assembly, but other antenna assemblies, e.g., monopole or leaky wave antenna assemblies, may also utilize the principles set forth herein. Located at the distal end of the antenna assembly 112 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien. The end cap or tapered portion 120 may include other shapes, such as without limitation, a tip 123 that is rounded, flat, square, hexagonal, or cylindroconical.

In some variations, the antenna assembly 112 includes a distal radiating portion 105 and a proximal radiating portion 140. In some embodiments, a junction 130 couples the proximal radiating portion 140 and the distal radiating portion 105. In some embodiments, the distal and proximal radiating portions 105, 140 align at the junction 130, which is generally made of a dielectric material, e.g., adhesives, and are also supported by the inner conductor that extends at least partially through the distal radiating portion 105. In some embodiments, the antenna assembly 112 may be provided with a coolant chamber (not shown). Additionally, the junction 130 may include coolant inflow and outflow ports (not shown) to facilitate the flow of coolant into, and out of, the coolant chamber. In some embodiments, the antenna assembly 112 may be provided with an outer jacket (not shown) disposed about the distal radiating portion 105, the junction 130 and/or the proximal radiating portion 140. The outer jacket may be a water cooled catheter formed of a material having low electrical conductivity.

During microwave ablation, e.g., using the electrosurgical system 10, the probe 100 is inserted into or placed adjacent to tissue and microwave energy is supplied thereto. Probe 100 may be placed percutaneously or atop tissue, e.g., using conventional surgical techniques by surgical staff. A clinician may pre-determine the length of time that microwave energy is to be applied. The duration of microwave energy application using the probe 100 may depend on the progress of the heat distribution within the tissue area that is to be destroyed and/or the surrounding tissue.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Ablation volume is correlated with antenna design, antenna performance, number of energy applicators used simultaneously, ablation time and wattage, and tissue characteristics, e.g., time impedance.

In operation, microwave energy having a wavelength, lambda ($\lambda$), is transmitted through the antenna assembly 112, e.g., along the proximal and distal radiating portions 140, 105, and radiated into the surrounding medium, e.g., tissue. The length of the antenna for efficient radiation may be dependent on the effective wavelength, $\lambda_{eff}$, which is dependent upon the dielectric properties of the treated medium. Antenna assembly 112 through which microwave energy is transmitted at a wavelength, $\lambda$, may have differing effective wavelengths, $\lambda_{eff}$, depending upon the surrounding medium, e.g., liver tissue, as opposed to breast tissue.

Figure 4:
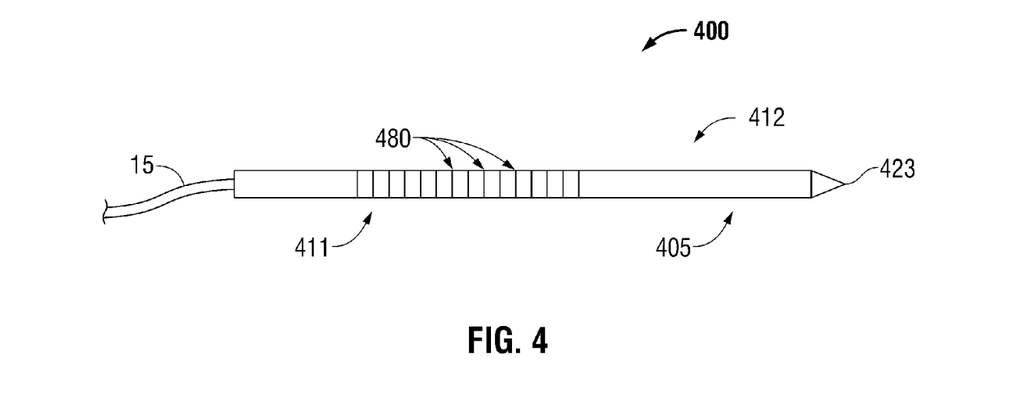
FIG. 4 is a schematic diagram of an energy applicator with indicia graduation marks according to an embodiment of the present disclosure.

According to an embodiment of the present disclosure, an energy applicator shown generally as 400 in FIG. 4 includes an antenna assembly 412 having a radiating portion 405 connected by a feedline 411 (or shaft) via a transmission line 15 to an energy source (e.g., 28 shown in FIG. 3). The energy applicator 400 includes a plurality of indicia graduation marks 480 disposed on at least a portion of the antenna assembly 412 and/or the feedline 411. The indicia graduation marks 480 may be etched, stamped, formed or the like, and may be disposed in fixed relationship with a known point on the antenna assembly 412, such as without limitation, the distal tip 423.

The visual assistance provided by the indicia graduation marks 580 may allow the surgeon to selectively position the antenna assembly 412 in tissue. Antenna assembly 412 is similar to the antenna assembly 112 shown in FIG. 3, except for the indicia graduation marks 480, and further description thereof is omitted in the interests of brevity. The shape and size of the indicia graduation marks 480 may be varied from the configuration depicted in FIG. 4.

Figure 5:
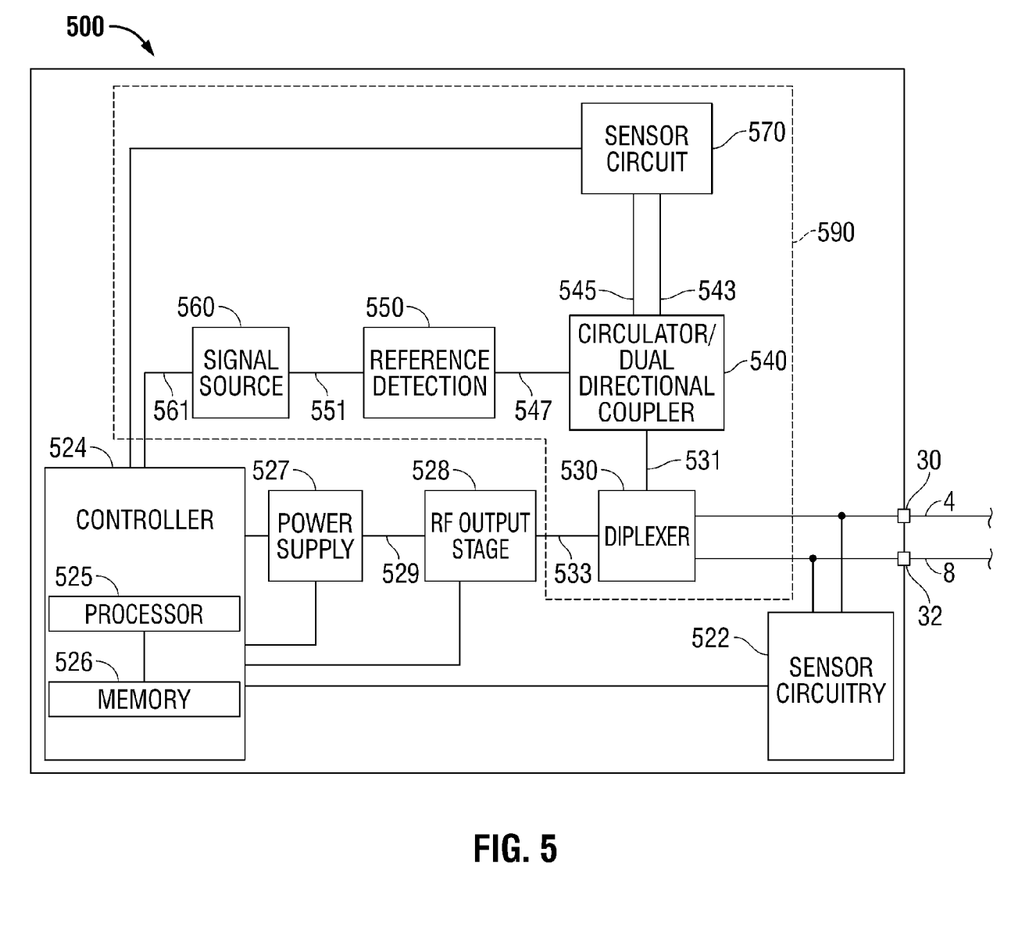
FIG. 5 is a schematic block diagram of an electrosurgical power generating source according to an embodiment of the present disclosure.

FIG. 5 schematically illustrates an electrosurgical power generating source (shown generally as 500) according to an embodiment of the present disclosure including a controller 524, a DC power supply 527, and a data acquisition module 590. Data acquisition module 590 includes a diplexer 530 and a circulator/dual directional coupler 540. In some embodiments, as shown in FIG. 5, the electrosurgical power generating source 500 includes a signal source 560 coupled via a transmission line 561 to the controller 524.

The DC power supply 527 is connected to an AC power source (not shown) and includes a high-voltage DC power supply, e.g., to provide high-voltage DC power via a transmission line 529 to an RF output stage 528 of the power generating source 500, and may include a low-voltage power supply, e.g., to provide power to various components of the power generating source 500 (e.g., input controls, displays, etc.).

RF output stage 528 converts the high-voltage DC power into RF energy. The RF energy output by the RF output stage 528 is supplied via a transmission line 533 to a diplexer 530. The diplexer 530 is a multi-port network. In some embodiments, as shown in FIG. 5, the diplexer 530 includes an input port electrically-coupled through the return terminal 32 of the power generating source 500 to the return line 8, and an output port electrically-coupled through the active terminal 23 to the supply line 4. The diplexer 530 combines two different frequencies together, e.g., into a common output. The diplexer 530 provides a low impedance electrical pathway (at the operating frequency of the RF output stage 528) from the transmission line 533 to the supply line 4 and the return line 8 while providing a high impedance electrical pathway from the transmission line 533 to the transmission line 531. The diplexer 530 also may provide low impedance (at the operating frequency of the sensor frequency) from the transmission line 531 to the supply line 4 and the return line 8 but maintain the high impedance from the transmission line 531 to the transmission line 533.

The RF output stage 528 is capable of generating waveforms (e.g., sinusoidal, square, or any type of AC waveform) of high RF energy. The RF output stage 528 may be configured to generate a plurality of waveforms having various duty cycles, peak voltages, crest factors, and other suitable parameters. Certain types of waveforms are suitable for specific electrosurgical modes. For instance, the RF output stage 528 may generate a 100% duty cycle sinusoidal waveform in cut mode, which is normally suitable for ablating, fusing and dissecting tissue. The RF output stage 528 may generate a 1-25% duty cycle waveform in coagulation mode, which is normally suitable for cauterizing tissue to stop bleeding.

In some embodiments, as shown in FIG. 5, the diplexer 530 is coupled via a transmission line 531 to a circulator/dual directional coupler 540.

The electrosurgical power generating source 500 may include a plurality of connectors to accommodate various types of electrosurgical instruments, such as without limitation, instrument 2 shown in FIG. 1, electrosurgical forceps 10 shown in FIG. 2, energy applicator 100 shown in FIG. 3, and/or energy applicator 400 of FIG. 4. The power generating source 500 may be configured to operate in a variety of modes such as ablation, monopolar and bipolar cutting coagulation, etc. The electrosurgical power generating source 500 may include a switching mechanism (e.g., relays) to switch the supply of electrosurgical energy, e.g., RF energy, between the connectors, such that, for instance, when the monopolar electrosurgical instrument 2 is connected to the power generating source 500, only the monopolar connector receives RF energy.

The controller 524 includes a processor unit 525 operably connected to a memory 526, which may be any device or medium that can store code and/or data). The processor unit 525 may include any type of computing device, computational circuit, or any type of processor or processing circuit capable of executing a series of instructions that are stored in a computer-readable storage medium (e.g., memory 526). In some embodiments, the processor unit 525 is communicatively coupled to the DC power supply 527 and/or the RF output stage 528 allowing the processor unit 525 to control the output of the power generating source 500. In some embodiments, the processor unit 525 is configured to control the output of the power generating source 500 according to open and/or closed control loop schemes.

Figure 9:
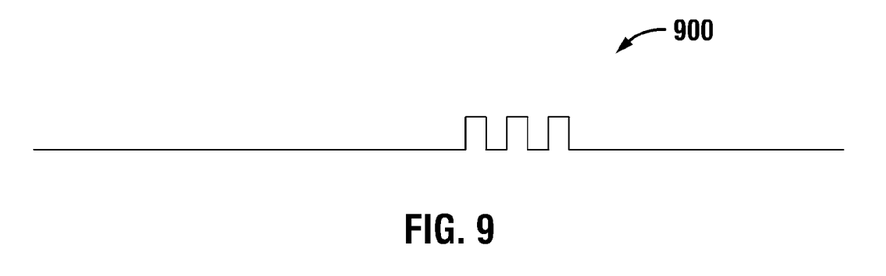
FIG. 9 is illustrates a reflected signal, such as a feedback signal of the detection source shown in FIG. 5, according to an embodiment of the present disclosure.

In a closed feedback control loop configuration, sensor circuitry 522 and/or the sensor circuit 570 may each include a plurality of sensors. In some embodiments, the sensor circuitry 522 may be the main sensor in the feedback control loop. The sensor circuitry 522 may additionally be used in conjunction with the sensor circuit 570 for measuring a variety of tissue and/or energy properties (e.g., tissue impedance, tissue temperature, output current and/or voltage, voltage and current passing through the tissue, etc.) provide feedback to the controller 524. The sensor circuit 570 may also be used to determine if the instrument (e.g., instrument 2 shown in FIG. 1, energy applicator 100 shown in FIG. 3, and/or energy applicator 400 of FIG. 4) is moving towards or away from the patient, using the Doppler theory of the frequency shift of the reflected signal 900 (FIG. 9). Based on one or more signals received by the controller 524 from the sensor circuitry 522 and/or sensor circuit 570, the controller 524 may signal the DC power supply 527 and/or the RF output stage 528 which, in turn, adjusts DC and/or RF power supply, respectively. The controller 524 may receive input signals from a user interface (e.g., user interface 81 shown in FIG. 6) and/or input controls (e.g., controls 83 shown in FIG. 6) associated with the power generating source 500 and/or input signals from an electrosurgical instrument, e.g., instrument 2. Based on the input signals, the controller 524 may adjust operating parameters of the power generating source 500 and/or perform other control functions, alarming functions, or other functions in association therewith. Some examples of operating parameters associated with an electrosurgical power generating source 28 that may be adjusted include temperature, impedance, power, current, voltage, mode of operation, and duration of application of electromagnetic energy.

In some embodiments, as shown in FIG. 5, the data acquisition module 590 includes a reference detection 550 coupled via a transmission line 547 to the circulator/dual directional coupler 540 and coupled via a transmission line 551 to a signal source 560. The reflected signal 900 (FIG. 9) is separated from the sensor signal 800 (FIG. 8) by the circulator/dual directional coupler 540, this signal can be communicated via differential pairs 545, 543 to detection source 570 which may be adapted to analyze the signal, e.g., using an internal processor (not shown), and/or condition the signal (e.g., filtering noise) and send the signal to the controller 524. The reference detection 550 can split the sensor signal for reference to the reflected signal.

Figure 6:
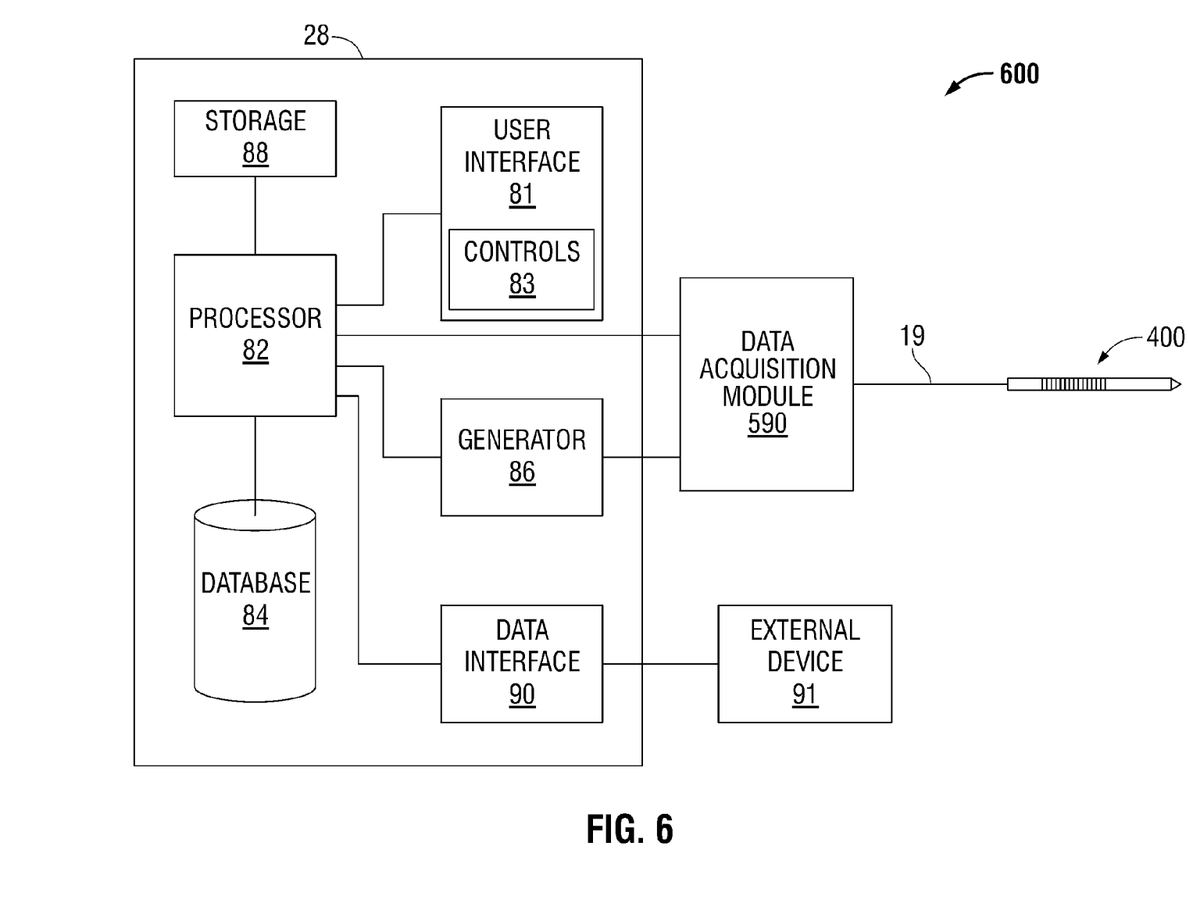
FIG. 6 is a schematic block diagram of an electrosurgical system according to an embodiment of the present disclosure.

FIG. 6 schematically illustrates an electrosurgical system (shown generally as 600) including an embodiment of the electrosurgical power generating source 28 of FIG. 3 that includes a generator module 86 in operable communication with a processing unit 82. Generator module 86 may be configured to provide various frequencies of energy. In some embodiments, the generator module 86 may be configured to provide energy at an operational frequency from about 300 MHz to about 10 GHz.

In some embodiments, as shown in FIG. 6, the data acquisition module 590 of FIG. 5 is coupled to the processing unit 82 and the generator module 86, and may be coupled to the energy applicator 400 of FIG. 4. It is to be understood, however, that other energy applicator embodiments (e.g., instrument 2 shown in FIG. 1, electrosurgical forceps 10 shown in FIG. 2, and energy applicator 100 shown in FIG. 3) may also be used. A suitable flexible, semi-rigid or rigid cable assembly 19 may be provided to electrically-couple the energy applicator 400 to the data acquisition module 590.

Processing unit 82 may be communicatively coupled to a user interface 81. User interface 81 may include a display (not shown), such as without limitation a flat panel graphic LCD (liquid crystal display). User interface 81 may additionally, or alternatively, include one or more controls 83 that may include without limitation a switch (e.g., pushbutton switch, toggle switch, slide switch) and/or a continuous actuator (e.g., rotary or linear potentiometer, rotary or linear encoder). In some embodiments, one or more controls 83 may have a dedicated function, e.g., display contrast, power on/off, and the like. One or more controls 83 may have a function that may vary in accordance with an operational mode of the electrosurgical power generating source 28.

In some embodiments, a storage device 88 is operably coupled to the processing unit 82, and may include random-access memory (RAM), read-only memory (ROM), and/or non-volatile memory (NV-RAM, Flash, and disc-based storage). Storage device 88 may include a set of program instructions executable on the processor 82 for executing a method for displaying and controlling ablation patterns in accordance with the present disclosure. Power generating source 28 may include a data interface 90 that is configured to provide a communications link to an external device 91. In an embodiment, the data interface 90 may be any of a USB interface, a memory card slot (e.g., SD slot), and/or a network interface (e.g., 100BaseT Ethernet interface or an 802.11 "Wi-Fi" interface). External device 91 may be any of a USB device (e.g., a memory stick), a memory card (e.g., an SD card), and/or a network-connected device (e.g., computer or server).

Processing unit 82 may include any type of computing device, computational circuit, or any type of processor or processing circuit capable of executing a series of instructions that are stored in a memory, e.g., storage device 88 or external device 91. Generator assembly 10 may also include a database 84 communicatively coupled to the processing unit 82 and configured to store and retrieve data, e.g., parameters associated with one or energy applicators (e.g., energy applicator 400). Parameters stored in the database 84 in connection with an energy applicator, or energy applicator array assembly, may include, but are not limited to, energy applicator (or applicator array assembly) identifier, energy applicator (or applicator array assembly) dimensions, a frequency, an ablation length (e.g., in relation to a radiating section length), an ablation diameter, a gap distance at the feed point (e.g. in relation to an ablation geometry), a temporal coefficient, a shape metric, and/or a frequency metric. Database 84 may be maintained at least in part by data provided by the external device 91 via the data interface 90. For example without limitation, energy applicator data and/or other data may be uploaded from the external device 91 to the database 84 via the data interface 90.

Figure 7:
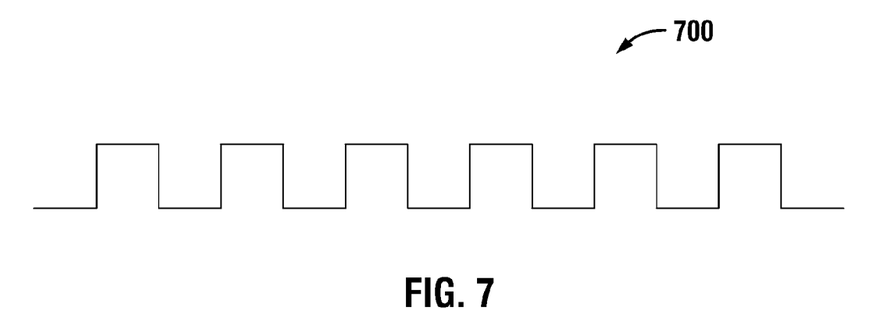
FIG. 7 illustrates a clocking signal, such as a continuous output of the RF output stage shown in FIG. 5, according to an embodiment of the present disclosure.
Figure 8:
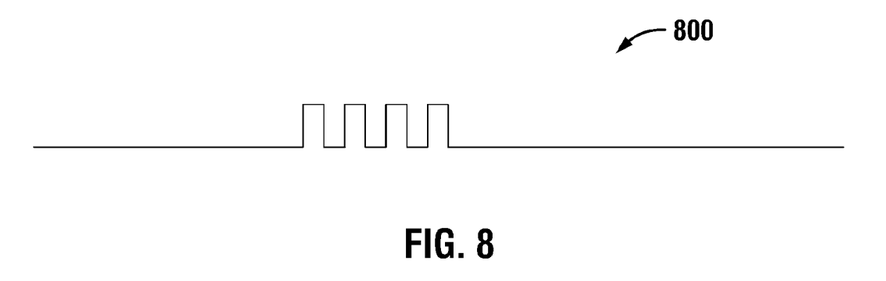
FIG. 8 illustrates a sensor signal, such as an input signal to the reference detection shown in FIG. 5, according to an embodiment of the present disclosure.

FIG. 7 illustrates a clocking signal 700, such as a continuous output of the RF output stage 528 shown in FIG. 5. FIG. 8 illustrates a sensor signal 800, such as an input signal to the reference detection 550 shown in FIG. 5. FIG. 9 illustrates a reflected signal 900, such as a feedback signal of the sensor circuit 570 shown in FIG. 5.

Figure 10:
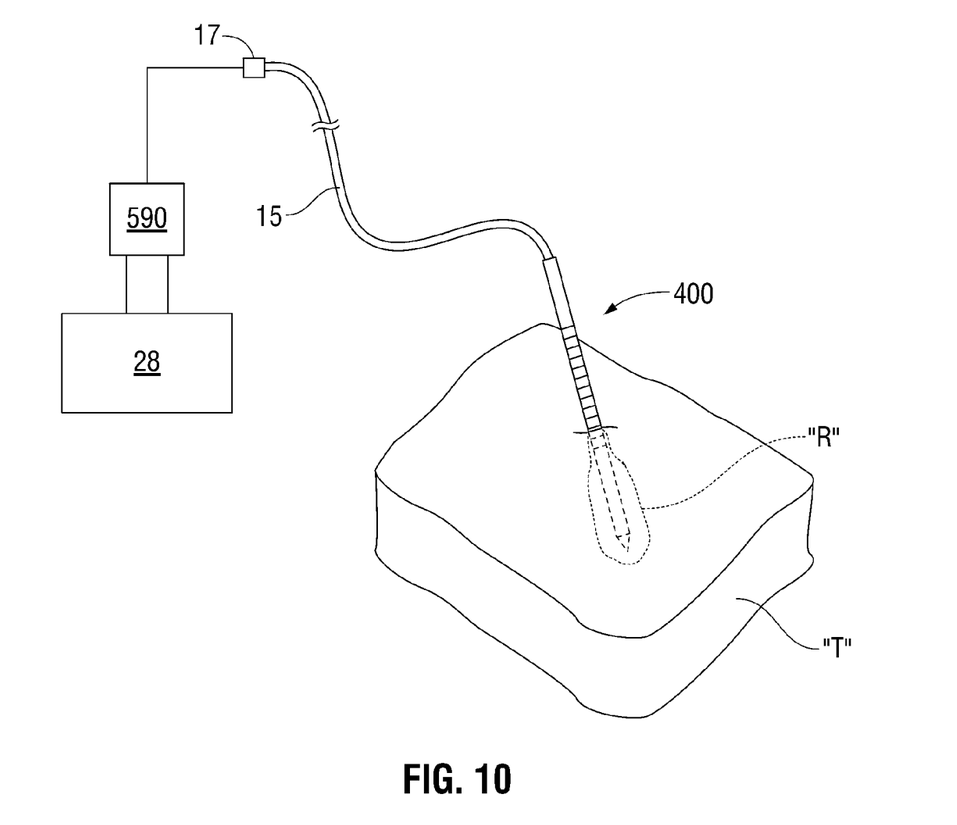
FIG. 10 is a diagrammatic representation of a radiation pattern of electromagnetic energy delivered into tissue by an energy applicator, such as the energy applicator of FIG. 4, in accordance with the present disclosure.

FIG. 10 shows a diagrammatic representation of a radiation pattern "R" of electromagnetic energy delivered into tissue "T" by the energy applicator 400 of FIG. 4. Energy applicator 400 may be placed percutaneously or surgically. Ultrasound or computed tomography (CT) guidance may be used to accurately guide the energy applicator 400 into the area of tissue "T" to be treated. The shape and size of the emitted radiation pattern "R" may be varied from the configuration depicted in FIG. 10.

In some embodiments, as shown in FIG. 10, the energy applicator 400 is coupled via a transmission line 15 to a connector 17, which further operably connects the energy applicator 400 to the data acquisition module 590 of FIG. 6 which, in turn is coupled to the electrosurgical power generating source 28. It will be understood, however, that other power generating source embodiments (e.g., power generating source 500 of FIG. 5) may also be used.

Hereinafter, methods of directing energy to tissue are described with reference to FIGS. 11 and 12. It is to be understood that the steps of the methods provided herein may be performed in combination and in a different order than presented herein without departing from the scope of the disclosure.

Figure 11:
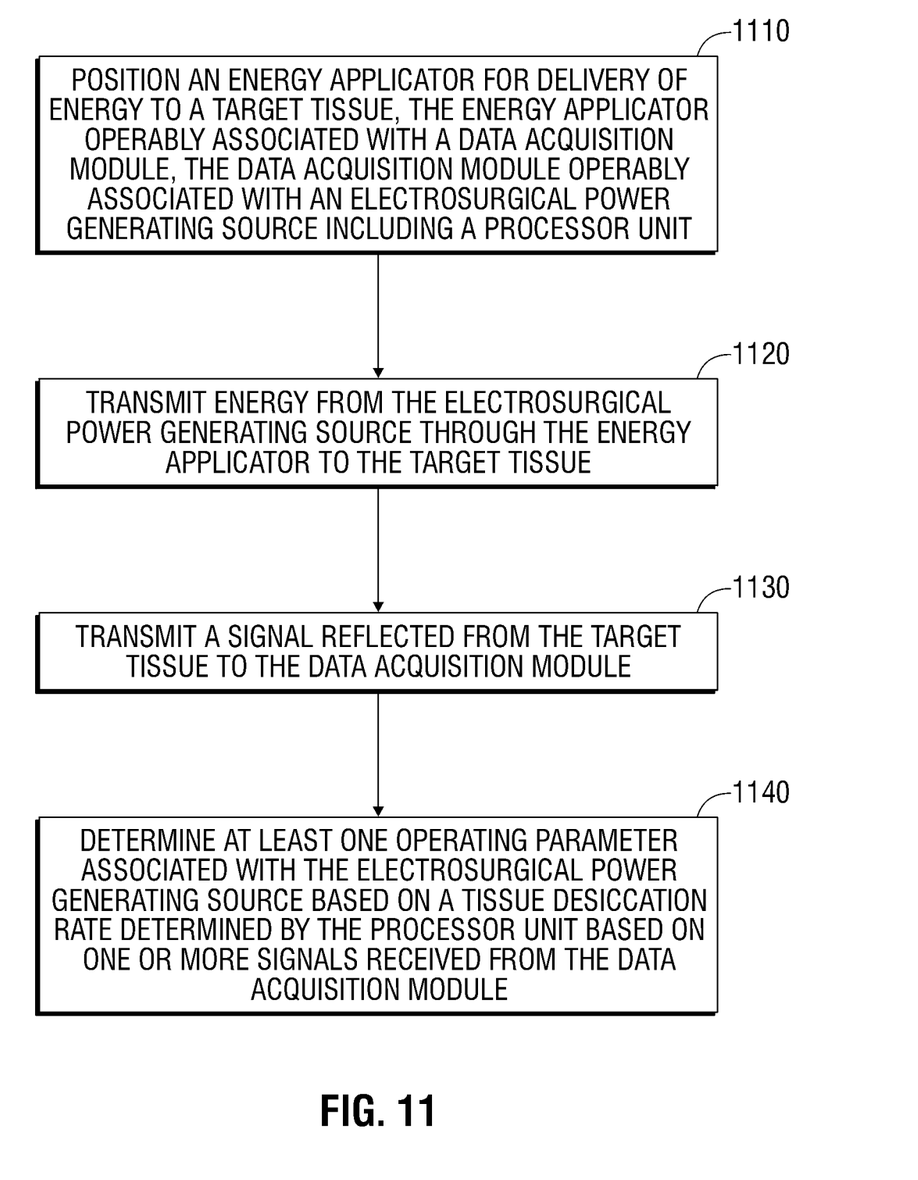
FIG. 11 is a flowchart illustrating a method of directing energy to tissue in accordance with an embodiment of the present disclosure.

FIG. 11 is a flowchart illustrating a method of directing energy to tissue according to an embodiment of the present disclosure. In step 1110, an energy applicator 400 is positioned for delivery of energy to a target tissue "T". The energy applicator may be inserted directly into tissue, inserted through a lumen, e.g., a vein, needle or catheter, placed into the body during surgery by a clinician, or positioned in the body by other suitable methods. The energy applicator 400 is operably associated with a data acquisition module 590. The data acquisition module 590 is operably associated with one or more components of an electrosurgical power generating source 28, such as without limitation, a processor unit 82.

In step 1120, energy from the electrosurgical power generating source 28 is transmitted through the energy applicator 400 to the target tissue "T". The electrosurgical power generating source 28 may be capable of generating energy at RF or microwave frequencies or at other frequencies.

In step 1130, a signal reflected from the target tissue "T" is transmitted to the data acquisition module 590. A cable assembly 19 may electrically-couple the energy applicator 400 to the data acquisition module 590.

In step 1140, one or more operating parameters associated with the electrosurgical power generating source 28 are determined based on a tissue desiccation rate which is determined by the processor unit 82 based on at least one signal received from the data acquisition module 590. Some examples of operating parameters associated with an electrosurgical power generating source 28 that may be determined include temperature, impedance, power, current, voltage, mode of operation, and duration of application of electromagnetic energy.

Figure 12:
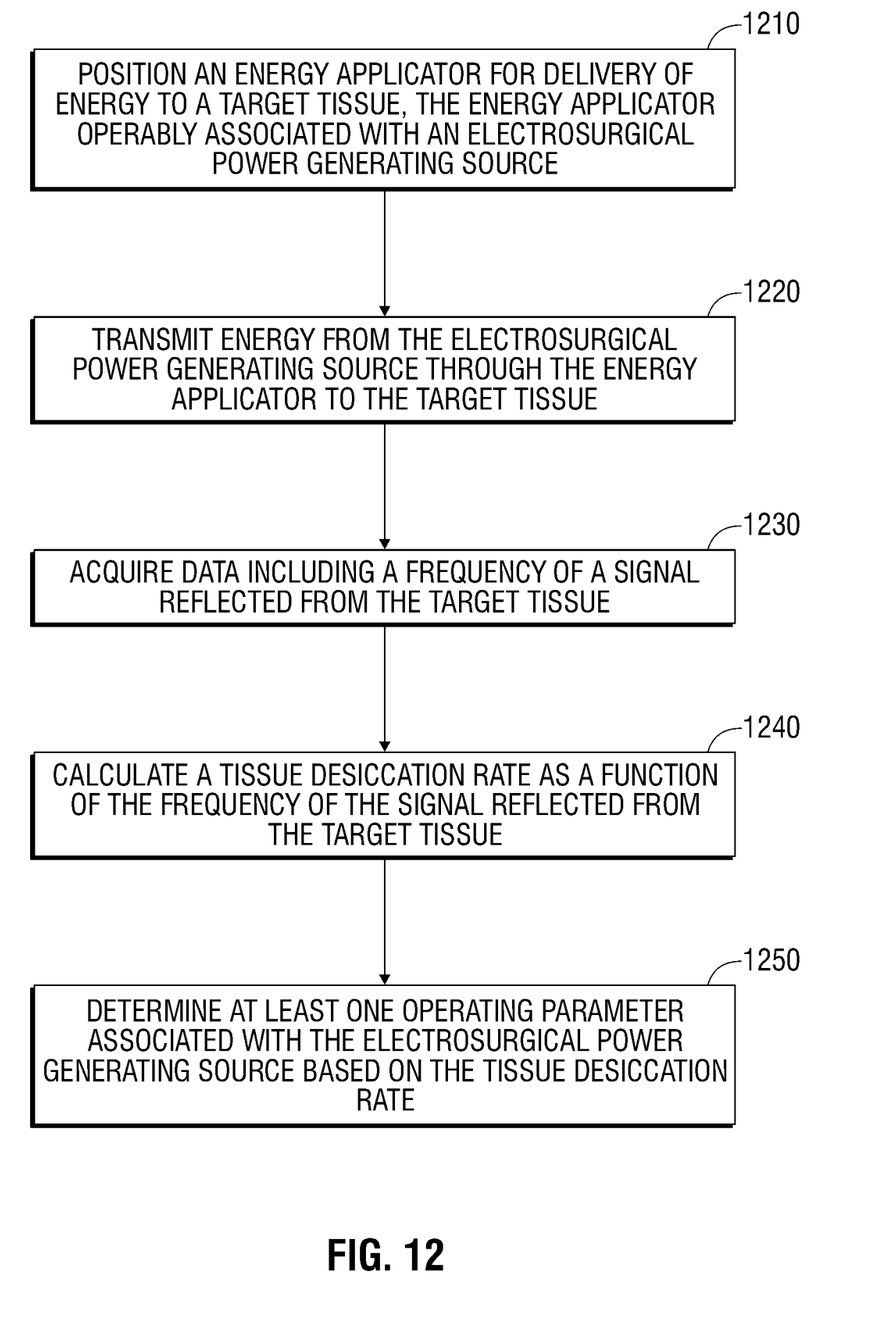
FIG. 12 is a flowchart illustrating a method of directing energy to tissue in accordance with another embodiment of the present disclosure.

FIG. 12 is a flowchart illustrating a method of directing energy to tissue according to an embodiment of the present disclosure. In step 1210, an energy applicator 400 is positioned for delivery of energy to a target tissue "T". The energy applicator 400 is operably associated with an electrosurgical power generating source 500.

In step 1220, energy from the electrosurgical power generating source 500 is transmitted through the energy applicator 400 to the target tissue "T".

In step 1230, data including a frequency of a signal reflected from the target tissue "T" is acquired.

In step 1240, a tissue desiccation rate is calculated as a function of the frequency of the signal reflected from the target tissue "T".

In step 1250, one or more operating parameters associated with the electrosurgical power generating source are determined based on the calculated tissue desiccation rate. In some embodiments, the position of the energy applicator may be adjusted based on the calculated tissue desiccation rate. For example, an energy applicator with a directional radiation pattern may be rotated either manually, or automatically, based on the calculated specific absorption rate, e.g., to avoid ablating sensitive structures, such as large vessels, healthy organs or sensitive membrane barriers.

The above-described electrosurgical systems for treating tissue and methods of directing energy to a target tissue may be suitable for various open and endoscopic surgical procedures.

In the above-described embodiments, signals reflected by a target tissue are transmitted from an energy applicator to a data acquisition module, which may be operably associated with one or more components of an electrosurgical power generating source. The above-described energy applicators may be inserted into or placed adjacent to tissue. The above-described data acquisition module receives a reflected signal and provides a signal that may be used to determine the rate of desiccation of tissue and/or to determine one or more operating parameters of an electrosurgical power generating source.

Various embodiments of the above-disclosed electrosurgical systems employ a secondary frequency, wherein the secondary frequency is different than the primary power source frequency, to determine a type of tissue, a condition of tissue, and/or a tissue response. In the above-described embodiments, a secondary frequency may be used to assist in determining when the energy applicator has been removed from the target tissue, which may trigger safety procedures and/or controls, e.g., control that reduces power level and/or shuts off the power delivery to the energy applicator.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical system, comprising:
    an electrosurgical energy source including an output stage;
    an energy applicator configured to couple to the electrosurgical energy source;
    a data acquisition module including a diplexer and a dual directional coupler, the data acquisition module separate from and operably coupled to the energy applicator, wherein the diplexer is configured to:
        receive a reflected signal generated by transmission of electrosurgical energy from the energy applicator to tissue;
        generate a first signal based on the received reflected signal;
        receive electrosurgical energy generated by the electrosurgical energy source from the output stage: and
        wherein the dual directional coupler is configured to receive the first signal and generate a second signal based on the first signal; and
    a processor operably coupled to the diplexer and the dual directional coupler of the data acquisition module and configured to calculate a desiccation rate based on the second signal and adjust electrosurgical energy output by the electrosurgical energy source based on the calculated desiccation rate.

2. The electrosurgical system of claim 1, wherein the reflected signal is transmitted by the energy applicator to the data acquisition module.

3. The electrosurgical system of claim 1, wherein the energy applicator includes a microwave antenna.

4. The electrosurgical system of claim 1, wherein the processor is configured to control at least one operating parameter of the electrosurgical energy source based on the calculated desiccation rate.

5. A method for monitoring tissue desiccation, comprising:
    applying electrosurgical energy to tissue via an energy applicator to generate a reflected signal;
    transmitting the reflected signal to a diplexer of a data acquisition module, wherein the data acquisition module is separate from the energy applicator;
    generating, with the diplexer, a first signal based on the reflected signal;
    receiving, with a dual directional coupler of the data acquisition module, the first signal;
    generating, with the dual directional coupler, a second signal based on the first signal;
    calculating a desiccation rate based on the second signal; and
    adjusting the applied electrosurgical energy based on the calculated desiccation rate.

6. The method of monitoring tissue desiccation of claim 5, further comprising controlling at least one operating parameter of an electrosurgical energy source coupled to the energy applicator based on the calculated desiccation rate.

7. The method of monitoring tissue desiccation of claim 5, wherein applying electrosurgical energy to the tissue via the energy applicator includes applying microwave energy to tissue via the energy applicator.

* * * * *